United States Patent [19]

Dureau

[11] Patent Number: 4,936,846
[45] Date of Patent: Jun. 26, 1990

[54] PANNUS FORMATION PREVENTING HEART VALVE

[75] Inventor: Georges Dureau, Francheville, France

[73] Assignees: Jean Cuilleron; Sarl Ceric, both of France

[21] Appl. No.: 187,724

[22] Filed: Apr. 29, 1988

[30] Foreign Application Priority Data

Apr. 29, 1987 [FR] France .................. 87 06347

[51] Int. Cl.$^5$ .................................. A61F 2/24
[52] U.S. Cl. ............................. 623/2; 137/533.19
[58] Field of Search ................... 623/2; 137/533.19

[56] References Cited

U.S. PATENT DOCUMENTS

| 1,381,078 | 6/1921 | Shevlin | 623/2 |
| 3,503,079 | 3/1970 | Smith | 137/533.19 |
| 3,601,877 | 8/1971 | Goosen | 623/2 |
| 3,858,246 | 1/1975 | Milo | 137/533.19 |
| 4,743,253 | 5/1988 | Maglardry | 623/2 |

FOREIGN PATENT DOCUMENTS 0806028 2/1981 U.S.S.R. ................... 623/2

Primary Examiner—Richard J. Apley
Assistant Examiner—Stephanie L. Iantorno
Attorney, Agent, or Firm—Eric P. Schellin

[57] ABSTRACT

The invention is relative to a cardiac valve.

This valve is of the type which comprises a means inserted with a controlled and limited clearance into a casing (2) comprising a ring (2.1) and a wire framework constituting arches, which ring comprises a peripheral groove (2.2) on its outer periphery which groove permits the centering and positioning of a covering (3), which valve is characterized in that said means which is inserted into the casing is a module comprising a hemisphere (1.1) extended in the front by a finger (1.3) which extends from the ring toward the outside, which ring comprises an inner profile (2.4) which forms a seat which permits the centering and angular tipping and the articulation of the module (1) in every position of the sweep of the finger.

2 Claims, 2 Drawing Sheets

PANNUS FORMATION PREVENTING HEART VALVE

BACKGROUND OF THE INVENTION

This invention relates to a heart valve.

FIELD OF THE INVENTION

Different types of valves, i.e. poppet, disc or ball type valves are known on the market. We wanted to improve the operating quality of these which are submitted to a considerable number of movements with time and within a particular medium in order to provide better blood flow and prevent any formation of thrombosis in the immediate environment of the valves.

SUMMARY OF THE INVENTION

According to a first feature, the heart valve is of the type comprising a valve means with a controlled and limited stoke inserted into a cage comprising a ring and a wire frame forming arches, the said ring having a groove on the external periphery enabling centering and positioning of a casing, the said valve being distinctive in that the said valve means, is a module comprising a semi-sphere extended at the front by a finger passing through the ring toward the outside, the said ring having an internal spherical profile forming a seat to center angularly tilt and articulate the module in any sweeping position of the finger. These features and others will appear as the specificication proceeds.

BRIEF DESCRIPTION OF THE DRAWINGS

In order to clarify the object of the invention without limiting it, the invention is illustrated by the accompanying drawings.

DETAILED DESCRIPTON OF THE INVENTION

Figure 1:
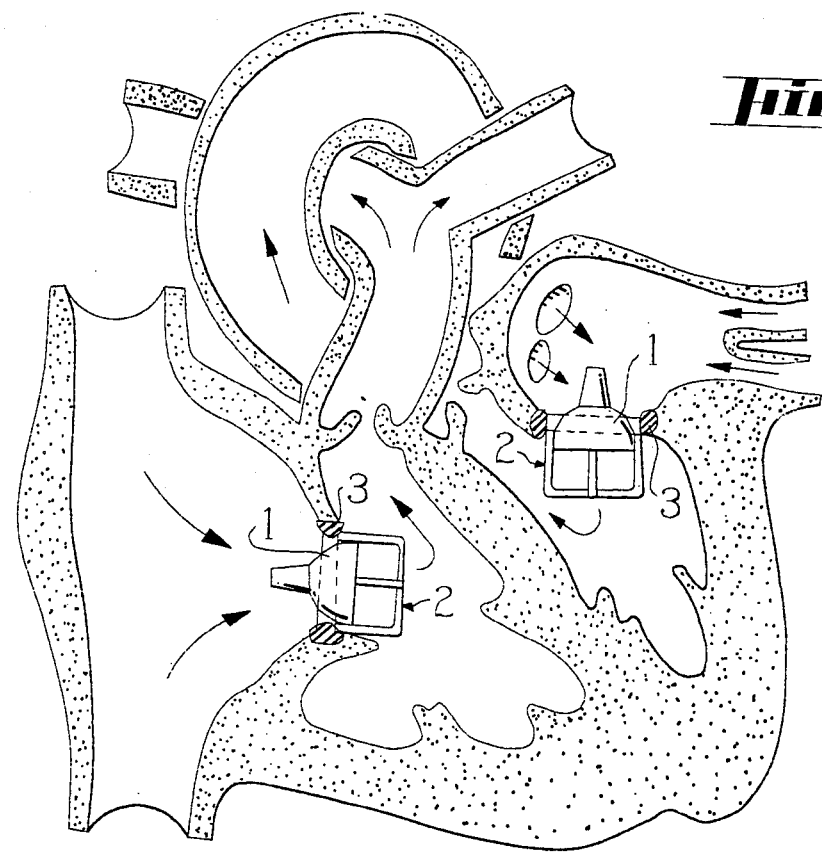
FIG. 1 is a sectional view of a human heart illustrating the positioning, according to two possible and non limitative positions of the valve according to the invention.
Figure 2:
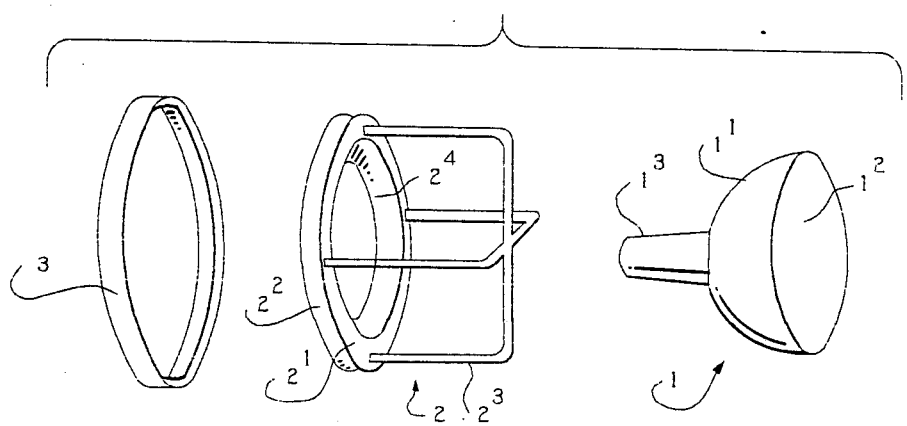
FIG. 2 is an exploded perspective view of the various elements making up the valve.

The object of the invention will become more apparent from the following non limitative description when considered in conjunction with the accompanying drawings. The valve comprises a means established under the form of a module (1) with a controlled and limited stroke, inserted into a cage (2). The latter comprises a profiled ring (2.1) with an external peripheral groove (2.2) in order to centre and position a casing (3) made from any suitable material, enabling it to be stitched up to the lips in front of the walls of the connecting hole between the auricle and the ventricle, for example. The said ring (2.1) is extended at the rear to form a cage with a wire frame (2.3) designed to include three or four U-shaped, flat bottom branches preferably forming arches. The cage thus produced is solid and made of any suitable material either with or without connecting points between the arches. According to the invention, the said cage contains a module (1) comprising a semi-sphere (1.1) with a flat, equatorial plane (1.2), extended by a finger (1.3) towards the front of the crowned end. This finger preferably has a truncated cone profile to provide a better blood flow. In addition, the internal peripheral part of the ring (2.1) is designed with a complementary spherical profile (2.4) for example which is non limitative, forming a seat for centering angular tilting and articulation of the module (1) on its semi-spherical seat part (1.1).

Figure 3:
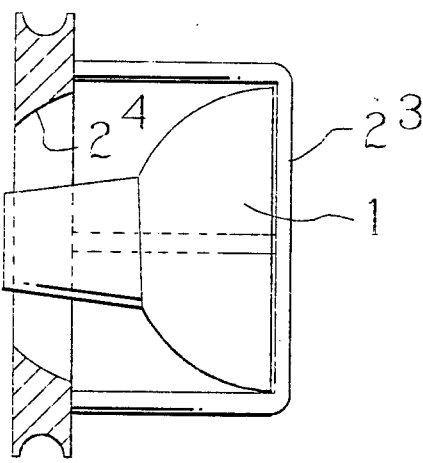

As shown in the drawings, when the valve is in the open position (FIG. 3), i.e. allowing the blood to pass, the module is applied against the bottom of the cage, whereas the finger (1.3) blocks the opening with the minimum of pressure with access through the ring; the front end of the finger substantially comes into the external transverse plane of the ring.

Figure 4:
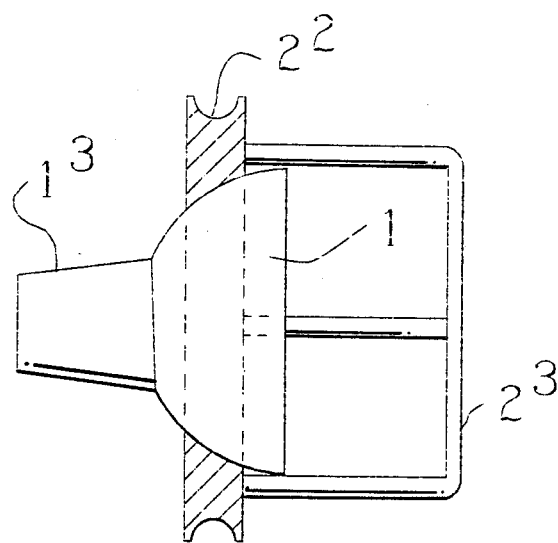
FIG. 3, 4, 5 and 6 are schematic views illustrating the various positions of the module with respect to the receiving cage.

In the closed position (FIG. 4), the module is applied against the seat (2.4) of the ring, thereby blocking the passage and preventing any circulation of blood, the finger (1.1) projecting outside.

Figure 5:
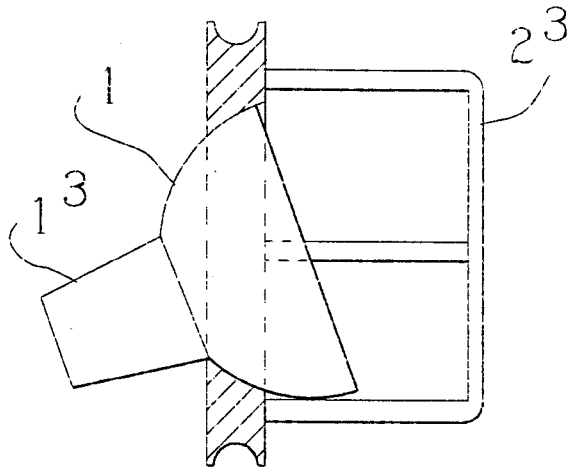
Figure 6:
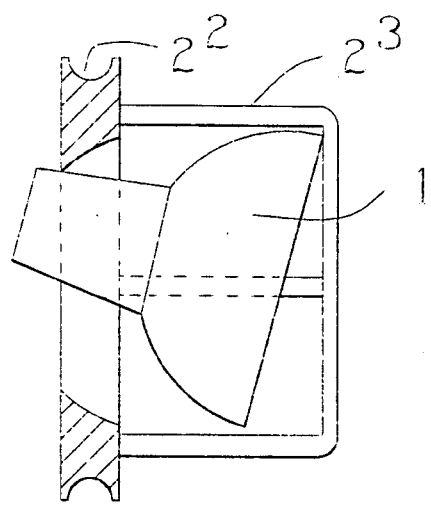

By referring to FIGS. 5 and 6, the module is found in an oblique position in the cage. The position illustrated in FIG. 5 on blockage limited by the finger (1.3) in the form of a truncated cone, is the most frequent position due to the fact of the asymmetry of the module and the weight of the truncated cone of the finger. The latter fully clears the aortic discharge chamber. The finer (1.3), comes into contact with the internal periphery of the ring by scraping along its surface, whereas the semi-spherical part is closely connected to the profile (2.4) inside the ring. The position illustrated in FIG. 6 of the module in the oblique position at the opening prevents dislocation as the finger (1.3) always abuts against the internal periphery of the ring. This position is generally instantaneously followed by positioning corresponding to FIG. 3. It is worth noting that the module cannot be removed from the cage once it has been fitted by any suitable technical process due to its shape. One of the new functions of this valve is that thanks to multiple positions of the finger, full sweeping over the whole opening of the valve at the atrium end is obtained which prevents the formation of pannus which may limit the valve opening. This pannus results from cellular growths likely to be formed around the ring from the stitched area of the casing and thus hinder the circulation of blood by gradually blocking the passage opening. The continuous sweeping provided by the movement of the finger of the module, thus enables a constant opening, free from undesired bodies, to be obtained. This new function of the module is particularly important and represents an undeniable improvement regarding the operation of the valve with time. In fact, according to the prior art, the poppet, disc or ball type valves do not have any likely way of projecting from the receiver ring and ensuring self-maintenance.

The module according to the invention as well as the other elements of the valve can be advantageously formed from, but not limited to pyrolytic carbon. The density of the module must be equal to that of the blood.

On the other hand, the cage of the valve according to the invention can be shorter with respect to a ball type valve, for example and therefore more compact, whilst providing greater movement of the module (1) than the ball valve. This additional movement gives an improvement in the flow through the ring which compensates for the loss of surface of the finger at the same level as the valve opening in the open position.

The advantages of the invention are quite apparent. The following characteristics are emphasized:

the reliable use of the valve, no thrombosis formation, frequently encountered at the poppet valve hinges, the most frequent clearance of the aortic discharge chamber when the valve is used in the mitral position, the constant sweeping of the valve opening at the atrium end preventing the formation of panus.

Thus, the valves produced according to the invention can be made in any suitable size and material.

I claim

1. Pannus formation preventing artificial heart valve comprising an inner ring, said inner ring having a wire frame extending axially from one side thereof thereby forming a tubular cage on said one side, said cage terminating in a cage wall, said inner ring having a radially outwardly facing annular peripheral groove, an outer ring adapted and constructed to be sutured in palce when said heart valve is implanted said outer ring having an inwardly radially facing convex portion detailed to mate with said annular peripheral groove of said inner ring whereby said outer ring supports said inner ring, valve module means positioned axially within said cage, said valve module means having a semi-spherical surface facing said inner ring and a flat equatorial planor surface facing ways from the inner ring and facing said cage wall, said valve module means having an annular sweepable finger extending axially from said semi-sperical surface and through said inner ring to the side opposite of the cage, said inner ring having an internally extending profile forming a seat for centering and articulating said valve means, said cage being axially dimensioned and said valve module means being dimensioned whereby at least a portion of said finger extends to said side opposite of the cage of the inner ring even when said flat equatorial planar surface of the valve module means is in confrontation with said cage wall.

2. The panus formation preventing heart valve of claim 1 wherein said finger is in the form of a truncated cone.

* * * * *